April 2, 1974 L. W. LARSON Re. 27,957

BI-VALVED CAST

Original Filed Dec. 2, 1968

INVENTOR.
LEIGHTON W. LARSON
BY
ATTORNEY

United States Patent Office

Re. 27,957
Reissued Apr. 2, 1974

27,957

BI-VALVED CAST

Leighton W. Larson, Waconia, Minn.

Original No. 3,580,248, dated May 25, 1971, Ser. No. 780,335, Dec. 2, 1968. Application for reissue Dec. 15, 1971, Ser. No. 208,487

Int. Cl. A61f *5/04*

U.S. Cl. 128—89 11 Claims

Matter enclosed in heavy brackets [ ] appears in the original patent but forms no part of this reissue specification; matter printed in italics indicates the additions made by reissue.

ABSTRACT OF THE DISCLOSURE

A cast for immobilizing broken limbs which includes a pair of bivalved shells, an inflatable liner in each of the shells, an absorbent liner or padding, and means for releasably securing the bivalved shells together. The cast is reuseable, permits convenient visual inspection of the broken limb without destruction of the cast, and provides for adjustment of the volume of the inside cavity and the pressure on the immobilized limb through adjustment of the inflatable liners.

BACKGROUND OF THE INVENTION

The invention relates to the field of immobilizing broken limbs and other body parts through the use of a cast or splint. The customary means of immobilizing a broken limb is the plaster-of-Paris cast which is not reuseable, does not provide for visual access without the destruction thereof, and which cannot be adjusted to compensate for swelling and contraction of the immobilized limb.

There have been a number of efforts to depart from the traditional plaster-of-Paris cast in favor of a lighter, reuseable and adjustable cast. There have also been efforts to make casts which may open for visual inspection of the limb, and close when the inspection is completed. None of these prior art devices, however, offer the advantages of the present invention.

The Ramirez patent U.S. Pat. No. 3,032,033, for example, discloses a resin-impregnated fiberglass shell which includes two halves which are secured together to form a cast which conforms to the shape of the limb to be immobilized. The Ramirez cast, however, does not include any means for adjusting or compensating for the difference in configuration between the limb and the shell of the cast. In other words, the rigid shell portion must be formed with extreme care to insure that it conforms accurately to the shape of the limb which is to be immobilized. The present invention, with its inflatable liner, provides for substantial adjustment to insure that the immobilized limb will be tightly held even though there may be differences in shape and size between the cast and the limb. Moreover, the present invention allows for continued adjustment to compensate for swelling or a decrease in size of the immobilized limb.

The Gottfried patent (U.S. Pat. No. 3,153,413) discloses an inflatable pressure bandage-splint which provides adjustability to compensate for swelling or decrease in size but it does not include a rigid outer protective shell. In addition the Gottfried bandage-splint provides for visual access and reclosing of the device. There is, however, a lack in uniformity in the thickness of the inflatable liner from a maximum thickness opposite the closure means to a complete lack of thickness at the closure means. The lack in liner thickness at the closure means along with the lack of a protective rigid outer shell limits the value of the Gottfried design to temporary or first-aid type applications.

Other substances have been disclosed for use in the formation of a cast such as plastic foam which is the subject of the Gibbons patent (U.S. Pat. No. 3,403,676). Although initially there is excellent conformance between the cast and the immobilized limb, *the Hoppe patent (U.S. Pat. No. 2,947,307) and the* Gibbons [splint does] *splints do* not include any means for adjusting the inside cavity of the splint as the immobilized limb swells or decreases in size.

SUMMARY

The present invention provides a bivalved cast which overcomes most of the problems of the prior art. The invention includes two rigid half shells which correspond generally to the body portion to be immobilized and which each have a generally channel-shaped cross section and mating edges which define a plane passing through the longitudinal axis of the body portion. An inflatable liner is disposed in each of the rigid shells and extends over substantially the entire inner surface. Means is provided exterior of the rigid shells for inflating each of the liners. A layer of absorbent material is placed inwardly of the liners to make direct contact with the immobilized limb. Means is provided for releasably joining the two shells to thereby form a protective cast which may be opened for visual access to the limb.

In addition to the provision of convenient visual access without destruction of the cast, the present invention makes adjustment of the cast a simple matter. More particularly, as the limb swells or contracts the pressure in the inflatable liners may be varied to compensate for the swelling or contraction and [the] thereby maintain a constant pressure on the limb. Moreover, pressure may be varied, within the limits necessary to immobilize the limb, to provide for individual patient comfort.

The bivalved cast of the present invention need not be formed to accurately conform to the shape of the body portion which is to be immobilized, since discrepancies may be readily compensated for by the inflatable liners. And finally the cast of the present invention is substantially lighter than most casts, particularly the plaster-of-Paris cast, yet provides equivalent protective and immobilization strength.

The primary object of the present invention is to provide a reuseable cast which may be opened for visual access to the immobilized limb without destruction of the cast and which includes means for adjusting the pressure between the cast and the limb.

*With these observations and objectives in mind, the manner in which the invention achieves its purpose will be appreciated from the following description and the accompanying drawing, which exemplifies the invention, it being understood that changes may be made in the specific structure disclosed herein without departing from the essentials of the invention set forth in the appended claims.*

*The accompanying drawing illustrates one complete example of the embodiments of the invention constructed according to the best mode so far devised for the practical application of the principles thereof, and in which:*

[BRIEF DESCRIPTION OF THE DRAWING]

In FIG. 1 the inflatable liner and absorbent material may be seen as well as one connection for inflating the liner.]

FIG. 2 also shows the means for releasably securing the two rigid shells together.

[DESCRIPTION OF THE PREFERRED EMBODIMENT]

Figure 1:
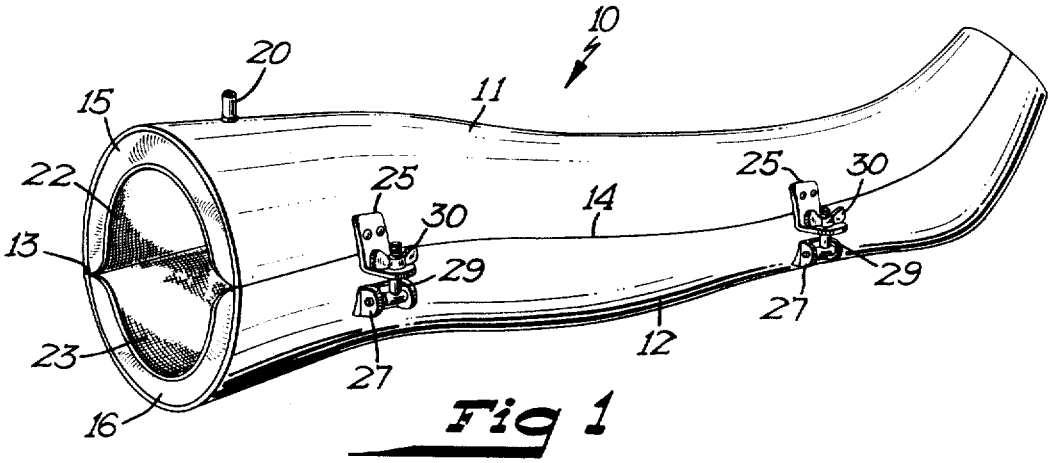
FIG. 1 is a perspective view of the bivalved cast which comprises the present invention, in its closed [position] *condition*, without association with the limb to be immobilized, *in this case the lower leg, for which it is intended.* [While a cast for the lower leg is shown, the present invention may be used for a number of other applications.

[The general nature of the preferred embodiment may be readily understood with reference to FIG. 1. The bivalved cast 10 which comprises] *Referring to the drawing, the numeral 10 designates generally the bivalved cast of* the present invention. *It comprises* [*includes*] an upper rigid shell 11 and a lower rigid shell 12. [Both] *The* shells 11 and 12 are [formed to conform] *complementary and coact to provide a rigid enclosure conforming* to the general shape of the body portion which is to be immobilized, in this case a leg. [and each] *Each* of the shells [have] *has* a generally channel-shaped cross section, *the two edges of which mate, as at 13 and 14, with the edges of the other shell.* [Each of the shells has two edges extending longitudinally thereof and which define a plane passing generally through the longitudinal axis of the immobilized limb. With reference to FIG. 1 the edges are shown in mated relationship at 13 and 14. Thus the edges (the point of contact between the upper rigid shell 11 and the lower rigid shell 12) define a plane passing through the longitudinal axis of the immibolized limb.]

Each of the shells is provided with an inflatable liner Liner 15 is nested in rigid shell 11 and liner 16 is nested in rigid shell 12. [Each of the inflatable liners 15 and 16] *These liners* extend over substantially the entire inner surface of rigid shells 11 and 12, respectively.

*A valve* [Value] 20 protrudes from rigid shell 11 to serve as a means for inflating liner 15. A similar valve 21 protrudes from lower rigid shell 12 to serve inflatable liner 15, as best as seen in FIG. 2.

*Layers* [A layer] of absorbent material such as sheet wadding 22 and 23 [is placed inwardly of] *line the inner walls of* inflatable liners 15 and 16, respectively to make direct contact with *and enwrap* the immobilized limb.

Figure 2:
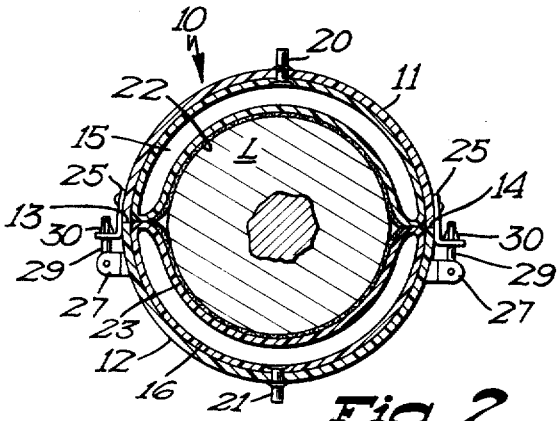
FIG. 2 is a *cross* sectional view of the cast shown in FIG. 1 and shows the upper and lower shell, the upper and lower inflatable liners, the absorbent padding material placed inwardly of the inflatable liner, and a sectional view of the immobilized limb, in this case a leg.
Figure 3:
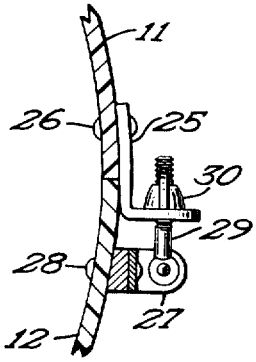
FIG. 3 is an enlarged sectional view of the means for releasably securing the two shell halves together; *and*

The means for releasably securing the rigid shells 11 and 12 *in mating* [is mated] relationship, as shown in FIGS. 1 and 2, includes a pair of fasteners on each side of each shell. Each fastener includes a bracket 25 secured to upper rigid shell 11 [such] as by rivets 26, most conveniently seen in FIG. 3. A lower bracket 27 is secured to lower shell 12 [such] as by rivets 28. [Threaded member] *A screw eye* 29 is pivotally secured to *each* lower bracket 27 and passes through *a slot in its companion* bracket 25 to accept wingnut 30 which is threaded thereto. Bracket 25 is offset downwardly with respect to joint 14 as best in FIG. 3. Bracket 25 thus serves to prevent lateral movement of rigid shell 11 with respect to rigid shell 12 when the bivalved cast is in its closed position. The pivotal connection between threaded member 29 and lower bracket 27 provides for opening of the bivalved cast through a hinging action without completely removing wingnuts 30 from threaded member 29 on one side of the cast.

While the specific embodiment shown is for immobilization of the lower leg from a point above the knee to a point below the heel, the bivalved cast which comprises the present invention may be used for a wide variety of other applications. More particularly, it may be formed with a rigid shell conforming in shape to other parts of the body so that it may be used for fractures of the calcaneus, metatarsals, fibulas, tibias, femur, fractures of the body of vertabres, fractures of vertrabral bodies, clavicular fractures, metacarpal fractures, etc. It is therefore contemplated that the present invention may be used as an upper leg cast, lower leg cast, an upper arm cast, a lower arm cast, a body spica, a foot cast, a neck cast, and a hand cast.

Rigid shells 11 and 12 may be formed [in] *of* a wide variety of substances, the primary requirements being radiolucence and adequate rigidity without excessive weight. Substances such as aluminum, resin-impregnated fiberglass and plastics may be used. Suitable commercial substances are sold under the trademarks Glaskyd, available commercially from American Cyanamid Company, Scotchply, available commercially from 3M Company, Bakelite, available commercially from Union Carbide Plastics Company and Durez, available commercially from Hooker Chemical corporation, Durez Plastics Division.

Inflatable liners 15 and 16 may be formed of rubber, plastic or other pliable material which is inflatable.

The [absorbent] layers of absorbent material 22 and 23 placed inwardly of inflatable liners 15 and 16 may be formed of gauze or sheet wadding or a sponge material.

Other means may be employed to releasably secure the two rigid shells together. A wide variety of fasteners may be used including the nonmetallic fastener sold under the trademark Velcro, a product available commercially which consists of mating hooked pile fabric forces.

The pressure in inflatable liners 15 and 16 should be 75 to 95 percent of diastolic pressure for best results. Such a pressure range provides substantial immobilization of the body portion and yet does not inhibit or prevent circulation of blood in the arteries and veins of the body portion in the cast.

Figure 4:
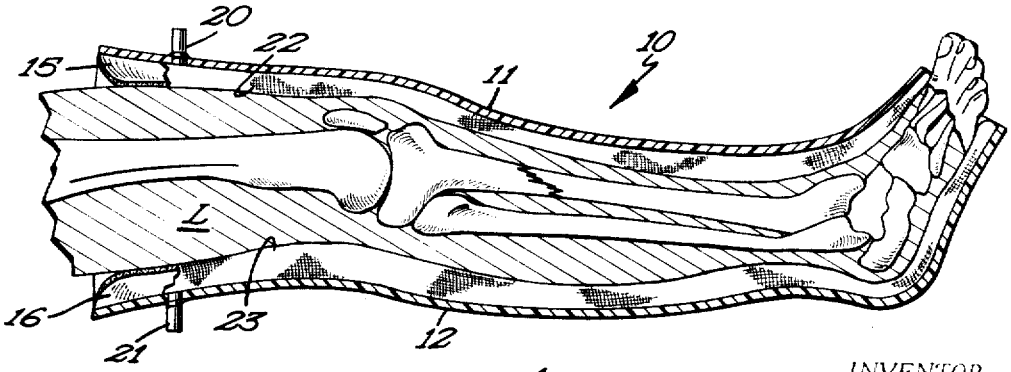
FIG. 4 is an axial sectional view of the cast and shows the relationship between the cast, the inflatable liners, the absorbent padding material, and the immobilized limb.

[The operation of the present invention may be readily understood with reference primarily to FIGS. 1 and 2. The rigid shells 11 and 12 are opened and the limb, L, is placed in the lower shell 12 and the upper shell 11 is closed. After shells 11 and 12 are secured in mated relationship, air is introduced into inflatable liners 15 and 16 through connections 20 and 21. A conventional pressure device may be readily employed to measure the pressure in the liners. Liners 15 and 16 provide a uniform pressure on the immobilized limb and automatically compensate for any variation in distance between the shell and the limb such as may be seen with reference to FIG. 4. As the limb swells or contracts the volume of air in liners 15 and 16 may be varied to maintain the limb under a constant pressure.]

*Although the operation of the invention is no doubt readily understood from the foregoing description and the drawing, for sake of completeness, in applying the cast to a limb, the limb L is placed in the lower shell 12 and then the upper shell 11 is closed upon the limb. After the shells are secured in mating relationship, air is introduced into the inflatable liners through the inlet valves 20 and 21. A conventional pressure gage may be employed to measure the pressure in the liners. The inflated liners provide a uniform pressure on the immobilized limb and automatically compensate for any variation in distance between the shells and the limb. As the limb swells or contracts, the volume of air in the liners may be varied to maintain the limb under a constant pressure.*

The cast may be opened to allow visual inspection of the limb without destroying the cast, *and when* [When] inspection and treatment is complete [is] *it* may be conveniently [closed] *reclosed.*

*The bivalved cast may be reused by simply removing and replacing the layers of absorbent material, following washing of the cast if needed.*

*Those skilled in the art will appreciate that the invention can be embodied in forms other than as herein disclosed for purposes of illustration.*

*The invention is defined by the following claims:*

[The bivalved cast 10 may be reused by simply removing the layers 22 and 23 of absorbent material followed by replacement with new material. The cast may also be washed if desired.

In conclusion, it may be seen that the present invention provides a novel bivalved cast which has significant advantages over the casts of the prior art.

Variations may be made in the form of the invention shown without departing from its scope which is to be limited only by the following claims.]

1. A bivalved cast comprising:

a first and second rigid shell corresponding in configuration to the body portion to be immobilized, each of said shells having a generally [channeled-shaped] *channel-shaped* cross section *with edges that mate with the edges of the other shell*; [and mating edges which define a plane passing through the longitudinal axis of said body portion;]

first and second inflatable *liners* [liner] disposed in said first and second rigid shells, respectively, and extending over substantially the entire inner surface thereof;

first and second means exterior of said first and second rigid shells for introducing air into said first and second inflatable liners, respectively;

[a first and second layer of absorbent material adapted to engage said body portion disposed inwardly of said first and second inflatable liners, respectively;] and means releasably joining said first and second rigid shells at said mating edges to thereby form a cast conforming in configuration to said body portion.

2. The cast of claim 1 wherein said first and second inflatable liners confine air under pressure in the range of 75 to 95 percent of diastolic pressure.

3. The cast of claim 2 wherein said mating edges on one side of said rigid shells are hinged together to thereby allow opening of one of said rigid shells with respect to the other for visual access to said body portion without destruction of said cast.

4. The cast of claim 3 wherein said first and second rigid shells are formed of rigid plastic material.

5. The cast of claim 4 and means for preventing lateral movement of said first rigid shell with respect to said second rigid shell when said shells are secured in mating relationship.

6. The cast of claim 5 wherein said first and second inflatable liners are adhesively secured to said first and second rigid shells, respectively.

7. The cast of claim 6, *further characterized by* [wherein said] first and second *layers* [layer] of absorbent material [is] adhesively secured to said first and second inflatable liners, respectively.

8. The cast of claim 7 and check valve means for allowing introduction of air into said liners and preventing deflation thereof.

*9. A cast for immobilizing a body portion, comprising:*

*(A) complementary separate rigid shells which coact when secured together to form a rigid cast conforming generally to the contour of the body portion to be immobilized;*

*(B) an inflatable liner in each of said rigid shells extending over substantially the entire inner surface thereof;*

*(C) air inlet means accessible at the exterior of said rigid shells through which their respective liners may be inflated; and*

*(D) means for separably securing said complementary rigid shells together.*

*10. The cast of claim 9, wherein there are two of said rigid shells, each of which is generally channel-shaped in cross section and has two edges which mate with those of the other shell.*

*11. The cast of claim 10, wherein said means for separably securing the rigid shells together comprises:*

*hinge means at one of the two mating edges, and disengageable means at the other two mating edges,*

*whereby upon disengagement of the latter means, said rigid shells may be swung open to afford access to the immobilized body portion.*

References Cited

The following references, cited by the Examiner, are of record in the patented file of this patent or the original patent.

UNITED STATES PATENTS

| | | | |
|---|---|---|---|
| 3,032,033 | 5/1962 | Ramirez | 128—90 |
| 3,351,055 | 11/1967 | Gottfried | 128—87 R |

LAWRENCE W. TRAPP, Primary Examiner

U.S. Cl. X.R.

128—Dig. 20